United States Patent [19]

Bolick

[11] Patent Number: 4,522,624
[45] Date of Patent: Jun. 11, 1985

[54] INCONTINENT PAD

[75] Inventor: Martha E. Bolick, Winnebago County, Wis.

[73] Assignee: Kimberly-Clark Corporation, Neenah, Wis.

[21] Appl. No.: 518,981

[22] Filed: Aug. 1, 1983

[51] Int. Cl.³ .............................................. A61F 13/16
[52] U.S. Cl. ................................................ 604/385 R
[58] Field of Search ............... 604/385, 386, 397, 387, 604/394, 393, 396, 358

[56] References Cited

U.S. PATENT DOCUMENTS

| 2,366,002 | 12/1944 | Carden | 604/386 |
|---|---|---|---|
| 2,718,888 | 9/1955 | Mevoney | 604/386 |
| 2,815,026 | 12/1957 | Meyer | 604/386 |
| 3,029,816 | 4/1962 | Neils | 604/385 |
| 3,150,663 | 9/1964 | Comles | 604/386 |
| 3,794,033 | 2/1974 | Ryan . | |
| 4,182,334 | 1/1980 | Johnson . | |
| 4,258,440 | 3/1981 | McGowan . | |
| 4,327,732 | 5/1982 | Thinnes . | |

FOREIGN PATENT DOCUMENTS 1114255  5/1968  United Kingdom ................ 604/397

Primary Examiner—John D. Yasko
Assistant Examiner—Christa K. Scott
Attorney, Agent, or Firm—Paul A. Leipold; James P. O'Shaughnessy

[57] ABSTRACT

An incontinent pad, for wearing as a bed protector about the hips and covering the perineal area of a wearer, is constructed of layers of absorbent and moisture impermeable layers. The pad is generally rectangular in shape, and has two symmetrical cuts extending from the longer portion of the pad toward the center, so as to divide the lower portion of the pad into a central hexagonal section which is folded to produce a breather moisture-retainer pouch, for juxtaposition near the urinary outlet of a wearer; and two triangular portions which are adjacent to the bed or other surface, the hexagonal portion is attached to the portion remaining under the patient, to form a seal along the thighs of the wearer for containment of moisture. The incontinent pad in use on a male or female wearer forms a bed protector with a thigh seal, offering a second line of defense against the escape of moisture.

23 Claims, 7 Drawing Figures

INCONTINENT PAD

BACKGROUND OF THE INVENTION

This invention relates to an incontinent pad. More particularly, this invention relates to an incontinent pad adapted to be worn as a bed protector about the hips and to cover the perineal area of a wearer. The size of the pad can be varied so as to range from that which is appropriate for newborn babies up to a size that is appropriate for larger adults who have experienced a loss, or at least a temporary loss, of the ability to control the normal excretory or urinary body processes.

Various means are known in the art for protecting bedding and other surfaces from urinary and bowel discharges. Products designed to meet these protection needs fall generally into three categories: bed protectors, full-size diapers, or secured padding.

Each of these devices has disadvantages for some users or in some circumstances.

Bed protectors are reusable or disposable bed pads or under pads. Bed protectors are essentially two dimensional coverings which are placed over the bed mattress and usually over the bottom sheet as well, but provide no protection to surfaces over the user, such as top sheets and other bedding. Effectiveness of bed protectors is also related to the user being appropriately placed, preferably centered, on the absorbent surface, so that the urine contacts and is retained by the absorbent material of the bed protector. Attempts at folding underpads, or pulling pads between legs of users, are often unsuccessful due to the absorbent medium not staying in place.

Full size (total wraparound) reusable or disposable diapers may be secured to the body by pins, snaps, tape or other securement means. These products provide an absorbent material in and around the crotch area and provide additional protection around the sides of the wearer by extending the absorbent material toward or around the sides, and the moisture-proof barriers around the sides. The resulting close containment of the body does not allow the skin to breathe, and may result in skin irritations such as diaper rash.

Furthermore, when these products are used by subjects lying down, fluid which escapes the boundaries of the product is deposited on the bedding.

Padding (for example, feminine napkins or incontinence insert pads) is held in place by securement means such as regular underwear, a variety of pad holders, straps, or other means. When used by persons who are lying down, absorbent padding placed loosely or held in the crotch area of the user does not provide protection at the sides of the product, a common source of leakage when used for nighttime containment.

Accordingly, an object of the present invention is to provide an incontinent pad adapted to be worn about the hips and to cover the perineal area of a wearer to provide better protection against escape of fluid from the incontinent pad.

SUMMARY OF THE INVENTION

These and other objects are provided, according to the present invention, by an incontinent pad adapted to be worn about the hips and to cover the perineal area of a wearer, comprising a layer of absorbent material and a moisture impermeable layer, having a generally rectangular shape, and having two symmetrical generally straight cuts through both layers, each cut extending from an opposite edge toward a generally centrally located point and terminating at a fold line generally perpendicular to the edges from which the cuts originate and located within the central third of the pad, measured along the edges from which the cuts originate, with the acute angle at the intersection of the cut line with the fold line extension ranging from about 15° to 75°.

DETAILED DESCRIPTION

The incontinent pad of the present invention comprises a layer of absorbent material and a moisture impermeable layer, both of which are per se known in the art. The absorbent material can be any of the cellulosic materials taught by the prior art for this purpose; the material described in Anderson et al. U.S. Pat. No. 4,100,324 is preferred. The moisture impermeable layer is likewise any plastic film known in the prior art for that purpose, such as polypropylene, polyethylene or similar plastic film.

Figure 1:
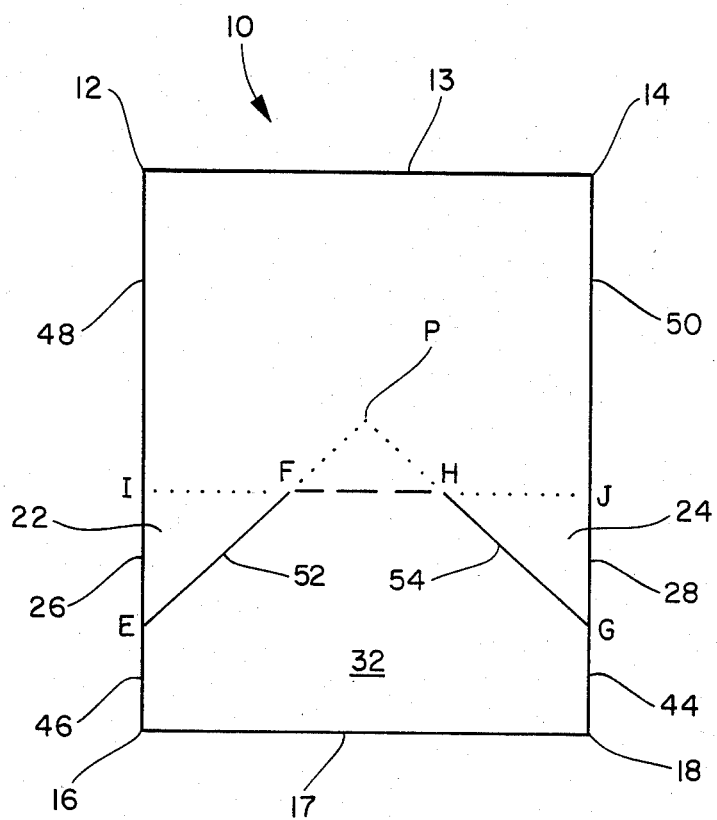
FIG. 1 is a plan view of an incontinent pad according to the present invention.
Figure 2:
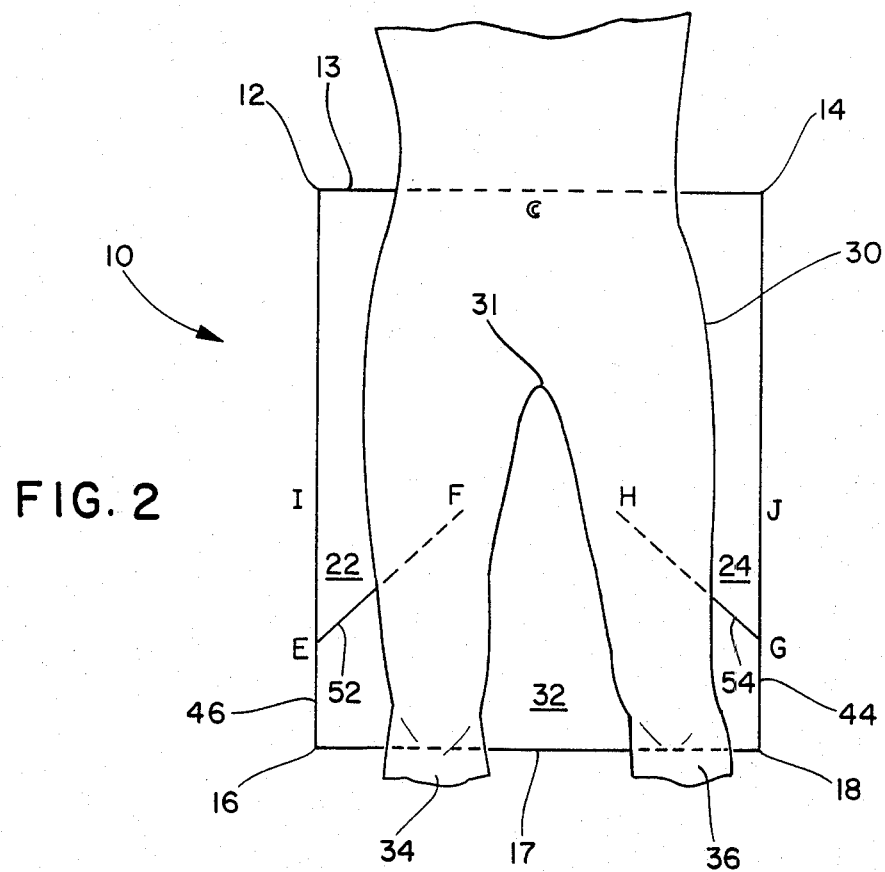
FIGS. 2-6 illustrate the incontinent pad of the invention in use.

The incontinent pad 10 of the present invention is described as being "generally rectangular" in shape. With reference to FIG. 1 of the drawings, the smaller dimension of the rectangular pad 10 between points 12 and 14 forming side 13 and between points 16 and 18 forming side 17 is construed as the width of the rectangle; while the longer dimension between points 12 and 16 and points 14 and 18, is construed as the length of the rectangle. "Generally rectangular" is to be construed as including minor variations on the rectangular shape, such as, for example, trapezoidal shapes in which the top width between 12 and 14 (as shown in FIG. 1), is longer than the bottom width 17 between points 16 and 18 or the top width between 12 and 14 is narrower than bottom width 17. It also includes pads in which the edges are somewhat irregular rather than straight.

The incontinent pad of the present invention is primarily intended for use by adults, but smaller sizes can be prepared for use by infants. Accordingly, the generally rectangular shape may have a width between about 10 and about 36 inches and a length between about 10 and about 40 inches.

The invention is particularly characterized by two cuts EF, GH, extending through both the layers of absorbent material and the moisture impermeable layer. The two cuts are preferably straight and generally symmetrical; i.e., the right cut GH is the same length as, and is opposite in position to, the left cut EF. Each cut originates at an opposite edge, which is the case of a rectangular pad 10 having a difference in the length and width, is preferably the longer edge, i.e., the length. Each cut extends from the longer edge generally toward a generally centrally located point P, which should be about halfway between edges 14-18 and 12-16, but need not be located halfway between edges 13 and 17.

The cuts terminate at a fold line FH which is generally perpendicular to the edges 12-16 and 14-18 from which the cuts EF and GH originate. The fold line FH is furthermore located within about the central third of the pad, measured along the edges from which the cuts originate; i.e., the distances 16 to I and 18–J are between one-third and two-thirds the distances of 12–16 and 14–18, I and J being the points at which the extension of fold line FH intersects edges 12–16 and 14–18, respectively.

The cuts EF and GH are positioned such that the angle—i.e. angle IFE and angle JHG, between the cut and the fold line extension is between about 15° and about 75°, preferably between about 30° and about 60°.

To state this a different way, the cut lines would form an angle at the central point of between about 150° and 30° and preferrably between about 120° and about 60° for comfort and good thigh sealing. The cuts are furthermore extended for a length such that the fold line FH is from one-sixth to one-half of the width of the pad, i.e., such that the fold line FH is between about 2 and about 12 inches in length, depending on the width of the pad. In a typical adult garment formed from a rectangular pad of about 24″ by 30″ the fold line length forming the crotch portion is preferably between about 6″ and about 8″ for ease of formation of the pad into the garment of the invention and good sealing at the legs of the wearer. While the cuts to form the garment of the invention are preferably generally symmetrical, it is not necessary that each cut angle be the same or mirror image of the other. The phrase "generally symmetrical" is to be construed as including opposite cuts of somewhat varied angle. The thigh seal formed at one leg is largely independent from the seal at the other leg and cuts of differing angle, are suitable as long as they are on opposite sides of the pad and directed toward generally the same point. However, it is preferred that the cuts be symmetrical for comfortable fit and looks.

As indicated, the width of the pad may vary from 10 to 36 inches. Preferred sizes for adults are a width from about 24 to about 28 inches, the length of the pad being from about 28 to about 36 inches for good bed protection, the fold line preferably is 6 to about 10 inches long and located from about 10 to about 16 inches from the base 17, i.e., the edge to which the fold line is parallel and which is nearer to the points E and G at which the cuts EF and GH originate. Dimensions presently contemplated as the best mode of carrying out the invention for adults, with good bed protection, are as follows: width 13 and 17 about 24 to about 28 inches, depending on the size of the adult; length 12–16, 14–18, about 30 inches; length of fold line FH about 8 inches; distance of fold line FH from edge 16–18 about 13 inches.

Use of the incontinent pad is illustrated in FIGS. 2–6. The triangular portions 22 and 24 within the outline of cuts EF and GH, extensions FI and HJ of fold line FH, and portions 26 and 28 of the edges from which the cuts originate, are each destined to become a leg extension. The bed protector is positioned with the moisture impermeable layer down, flat on a bed, with the triangular portions 22 and 24 next to the bed. An adult wearer 30 or any person intending to lie mostly on his or her back or side is positioned centrally on the bed protector, facing upward. Portion 32 bounded by cuts EF and HG edge 16–18 and fold line FH is destined to become the front of the bed protector for such individuals. However, for persons (particularly newborn babies) who spend most of their time on their stomachs, the person should be similarly positioned, but face down; in which case the portion 32 is destined to become the back of the bed protector.

Figure 3:
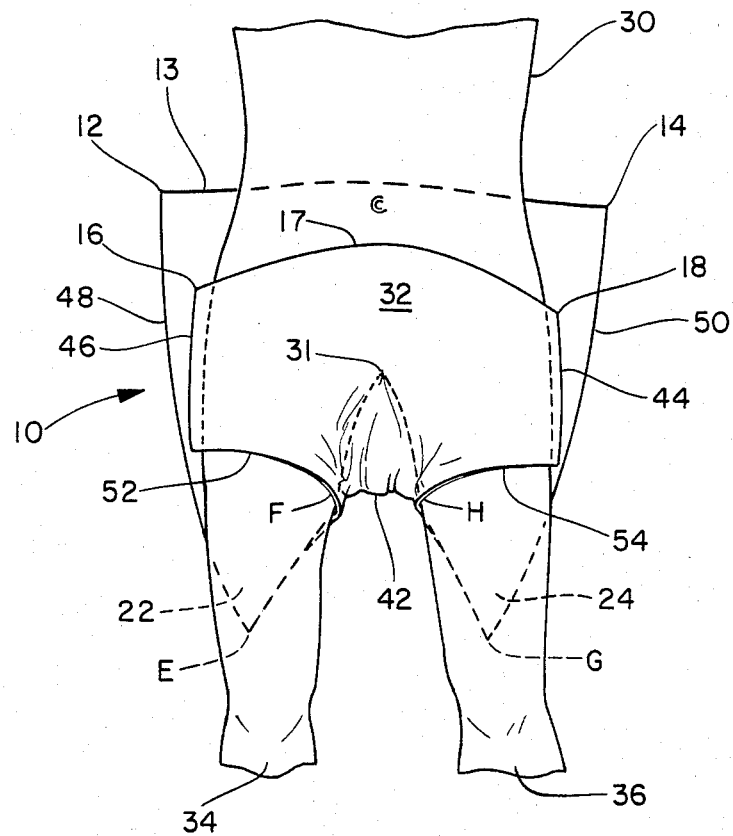
Figure 4:
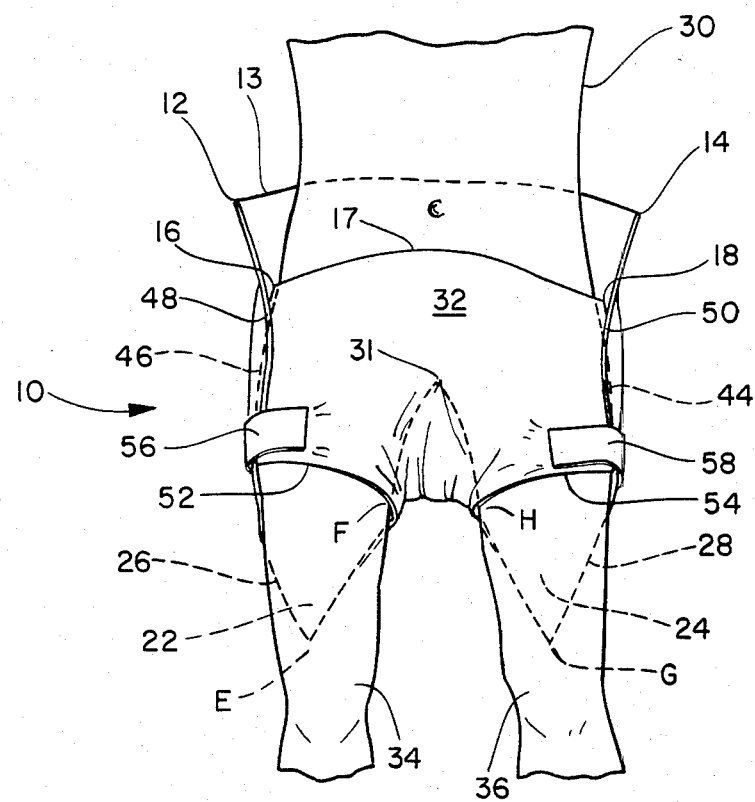
Figures 5, 7:
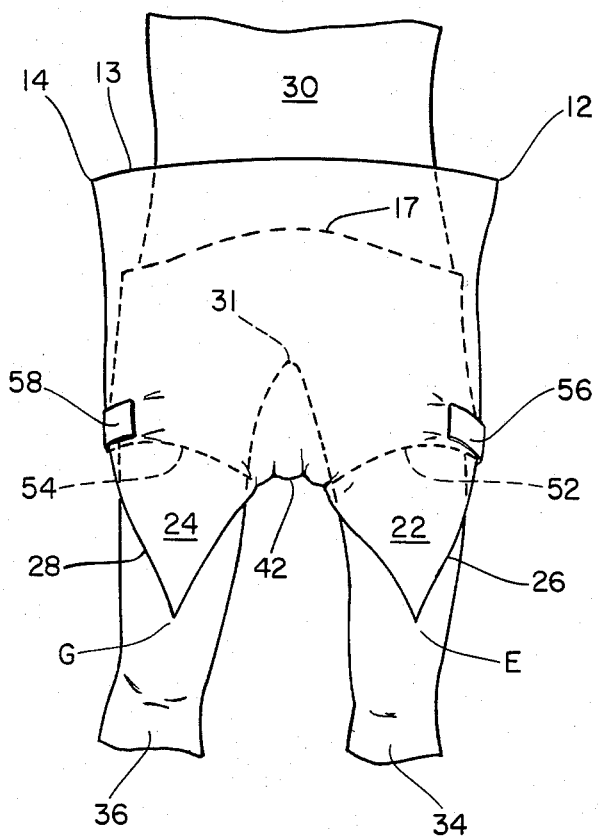
FIG. 7 is a plan view of an incontinence pad of the invention having embossed lines.
Figure 6:
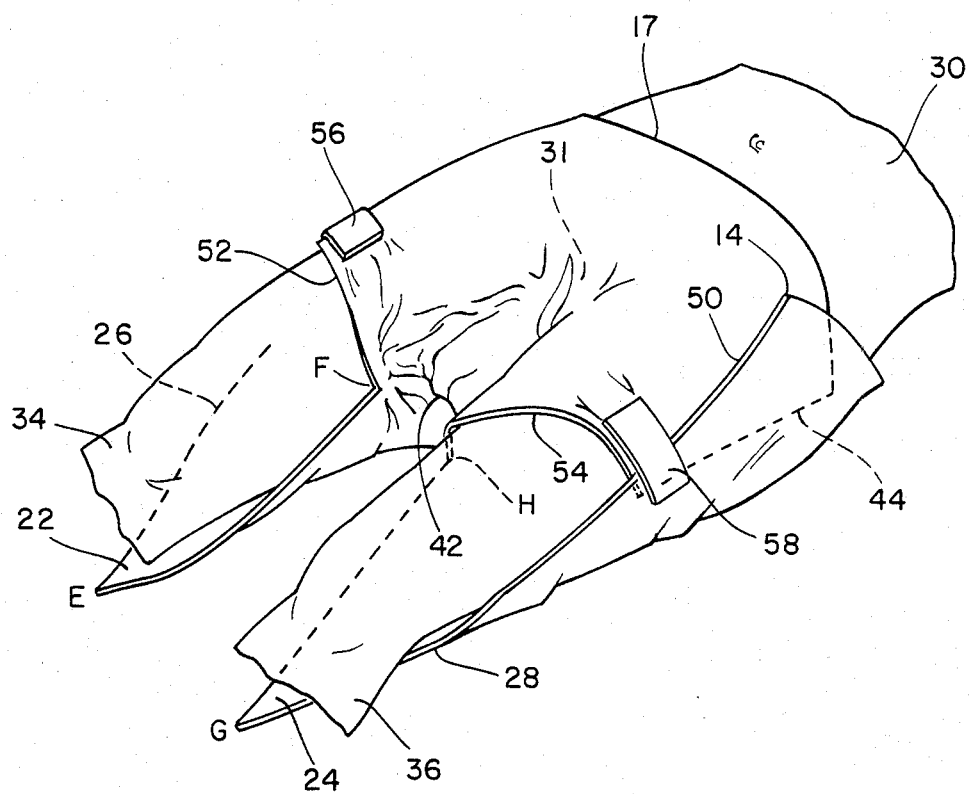

As shown in FIGS. 3 and 4, after the user is positioned on the protector, the hexagonal flap portion 32 of the pad 10 is pulled through the legs and folded upward to form the front of the protector with section FH (fold line) slightly gathered and placed between the legs 34 and 36. A clearance of 3″ to 6″ below the perineal area 31, is left between the pad and the wearer, thus forming the breather-retainer pouch 42. As shown in FIG. 6, the points F and H marking termination of cut lines are pulled higher than the bed or other surface to aid in leakage prevention. The gathering and pulling between the legs as indicated has the effect of moving the back leg extensions 22 and 24 under the legs. Sides 48 and 50 of the protector can then be folded over to meet sides 44 and 46 of front flap section 32 with edges 52 and 54 pulled taut and secured with tape 56 and 58 to form the thigh seals. The protector may also be secured at other points along sides 48 and 46 and sides 44 and 50 although such securement is not necessary to form the bed protector with thigh seal. In FIG. 5, which is a rear view of the pad fastened in place, it can be seen that the under portion has triangular pieces 22 and 24 pulled beneath the thigh when the thigh seal is formed while the edge 13 remains only slightly fitted to the body.

As shown in FIGS. 5 and 6, the final positioning of the incontinent pad, now formed into a bed protector garment, will have the triangular leg extension portions of the pad, 22 and 24, against the bed (not shown) and under the legs of the wearer.

The terminal portions of the cuts at F and H are positioned above the bed surface and generally against the inside of the legs of the wearer to prevent leakage.

The pad can be provided with adhesive means for holding the breather-retainer portion 42 in place; and with adhesive means for attachment of the triangular portions 22 and 24 to the thighs of the wearer. Generally, however, the invention does not require sealing except at the outer thigh points 56 and 58. The sealing at the outer thigh pulls the garment tight to prevent leakage around the thigh and maintains the ends of the cut portions above the bed surface to also minimize leakage.

The garments of the invention may be formed from pads having embossed or printed lines indicating where to cut to form garments. Such pads would allow the use of the invention pads as ordinary pads rather than only for garments. Such a pad is the pad 72 illustrated in FIG. 7. The pad has printed or embossed thereon cut lines 74, 76, 78 and 80 where cuts may be made to form the garment of the invention. For instance, lines 76 and 80 could be drawn on a 24″ by 30″ pad about 38° from the fold line extension to form a fold line of about 6″ in length between points 82 and 84 suitable for use on a small adult. Lines 74 and 78, drawn at about 41° from the fold line extension, could be used to form a cut pad with a fold line of about 8″ length between points 86 and 88 for use with a larger adult.

The garment of the invention may be fastened to the wearer by any convenient means. A suitable means is a tape such as surgical tape or masking tape. It is also possible that a tape fastener such as used on diapers having a removably covered adhesive section could be installed on the pad to allow the forming of the garment without tape present. However, this may be less preferred if not all pads were intended for use as garments, and also the variations in patient size may be more difficult to accommodate if the tape location is fixed.

In addition to the layer of absorbent material and the film of moisture impermeable layer, the pad of the present invention is preferably provided with an inner bodyside liner material, to insulate the body from the absorbent layers and any contained moisture. The product can also be made from a reusable base material consisting of a cloth absorbent layer with a moisture barrier attached.

The bed protector produced from the incontinent pad according to the present invention has the following advantages:

1. Waste is pulled away from the perineal area into a breather-retainer pouch 42 rather than held close to the skin of the perineal area as is characteristic of crotch-fitting pads and products. Skin can breathe and is less susceptible to irritation in sensitive perineal areas as waste is held away from the skin.
2. The proper folding and sealing of the protector at the thigh of the wearer maintains proper placement of the wearer on the absorbent medium, thus reducing opportunities for leakage which are observed to occur with flat bed pads and poorly-fitted garments and padding.
3. Unlike "diapers" which allow leakage onto surfaces if fluid escapes out of the sides and out of the primary crotch absorbent areas, the bed protector with thigh seal provides a second line of defense to leakage, by provision of the back leg extension portions of the pad.
4. The bed protector with thigh seal combines features of fit and containment normally found on wearable products with the additional protection beyond the crotch area normally found with bed pads.

EXAMPLES

Examples of incontinent pads having the configuration shown in FIG. 1 were tested by simulated use. These sheets (i.e., the material from which the incontinent pad was cut) were formed from underpads containing an absorbent material of 70/30 pulp/polymer blend, made in accordance with the teachings of U.S. Pat. No. 4,100,324. The weight of the absorbent portion of the material was either 120 or 170 grams per square meter. Dimensions tested were 28×30 inch and 24×30 inch of the 120 grams per square meter material, and 24×30 inches of the 170 grams per square meter material. The angles formed by the intersection of the cut lines EF and GH with the extension of the fold line was about 40°. The fold line FH was 8 inches long and 13 inches from the front edge 17 of the pad.

The product was tested through the artificial introduction of water (210 cubic centimeters at 12 cubic centimeters per second, to simulate a typical voiding into the breather retainer portion of the pad, using a model provided with an artificial delivery system. The pads were tested with nursing home patients with good results both for fit and functionality. The fold line width of 6" was found to give better fit to smaller adults than a fold line width of 8".

The product was found to offer good containment both in nursing homes and model tests, fluids were consistently concentrated toward the central portion of the product, thus reducing opportunities for leakage, and the triangular back leg extension portions were found to function properly by receiving fluids which escaped from the thigh seal area. There was no leakage onto the bedding surface when the 170 gram per square meter material was tested.

While the dimensions of the pad may be made wider and possibly longer to fit larger individuals, it is important to preserve the relationship of the front and back portions of the protector, the fold line FH, and the angles of the cutlines EF and GH with respect to the extensions of fold line FH to result in a product which for a given size of wearer will result in provision of the thigh seal, breather-retainer pouch and back leg extensions.

It should be understood that a wide range of changes and modification to the preferred embodiments described above can be made without departing from the scope of the present invention. For instance, while described for use with incontinent persons the invention also finds use in treatment of patients unable to be moved due to operations or injury. It is therefore intended that the foregoing detailed description be regarded as illustrative rather than limiting, and it is understood that it is the following claims, including all equivalents, which are intended to define the scope of the invention.

I claim:

1. An incontinent pad adapted to be worn about the hips and to cover the perineal area of a wearer, said pad comprising a layer of absorbent material overlaying a moisture impermeable layer, having a generally rectangular shape, and having two symmetrical generally straight cuts through both layers, each cut extending from a beginning at an opposite edge toward a generally centrally located point and terminating at a fold line generally perpendicular to the edges from which the cuts originate and located within the central third of the pad between the end points of the cuts, measured along the edges from which the cuts originate; with the angle of intersection of the cut line with the fold line extension ranging from 15° to 75°.

2. A pad according to claim 1, having a width between 10 and 36 inches and a length between 10 and 40 inches, the length being measured along the edges from which the cuts originate.

3. A pad according to claim 2, wherein the fold line at which the cuts terminate is placed from one-third to two-thirds of the length of the pad from the edge to which the fold line is generally parallel and which is nearer to the points at which the cuts originate.

4. A pad according to claim 3, wherein the angle of intersection of the cut line with the fold line extension is between about 30° and about 60°.

5. A pad according to claim 3, wherein the width of the pad is from about 24 to about 28 inches, the length of the pad is from about 28 to about 36 inches, the fold line is between about 6 and about 10 inches wide and from about 10 to about 16 inches from the edge to which the fold line is parallel and which is nearer to the points at which the cuts originate.

6. A pad according to claim 3, wherein the angle of intersection of the cut line with the fold line extension is about 40°, the width of the pad is about 24 inches, the length of the pad is about 30 inches, and the fold line is about 8 inches wide and about 13 inches from the edge to which the fold line is parallel and which is nearer to the points at which the cuts originate.

7. A pad according to claim 1 wherein securement means are provided to attach the front portion of the pad to the back portion of the pad to form the thigh seal.

8. A pad according to claim 7, wherein the pad is provided with adhesive means for holding the thigh sealing portion in place.

9. A method of forming a garment comprising providing a generally rectangular absorbent pad, forming cuts of generally equal length into the longer sides of said pad generally toward a central point, such cuts forming an angle with said central point of between 150° and about 30°, ending said cuts such that the end points of the cuts when joined form a fold line generally parallel to the shorter sides of said pad, placing the cut pad beneath a person in bed with said fold line between said person's legs and said cut lines under said person's thighs, pulling the end portion of the pad that includes the portion within the cut angle between said person's legs such that the ends of said cuts are above the bed and contacting the thighs of said person and joining the edges of the portion of the said end that includes said cut angle to the edges of the pad portion under the body of said person at the outer thigh to create a thigh seal.

10. The method of claim 9 wherein said portion between the cuts covers the perineal region.

11. The method of claim 10 wherein a breather-retainer pouch of between about 3 and about 6 inches depth is formed between said perineal region and said pad portion between said cuts.

12. The method of claim 10 wherein the pad portion under the person has triangular pad portions extending under the thighs.

13. The method of claim 10 wherein said angle of intersection of said cuts is between about 120° and about 60°.

14. A garment comprising an absorbent front portion, an absorbent crotch portion, and an absorbent back portion wherein said front and said back portions are joined at the outer thigh and said back portion has triangular extensions adapted to extend along the thighs of a wearer.

15. The garment of claim 14 wherein the outer side is formed of an impervious material.

16. The garment of claim 14 wherein said crotch portion is designed to be worn between about 3 and about 6 inches from the perineal region to form a breather-retainer pouch.

17. The garment of claim 14 wherein said triangular extensions extend along the back of the thigh of a wearer.

18. An incontinent pad that may be adapted to be worn about the hips and to cover the perineal area of a wearer, said pad comprising a layer of absorbent material overlaying a moisture impermeable layer, having a generally rectangular shape, and having two symmetrical generally straight cut indicator lines, each line extending from a beginning at an opposite edge toward a generally centrally located point and terminating such that the points of termination form a fold line generally perpendicular to the edges from which the lines originate and located within the central third of the pad between the end points of the lines, measured along the edges from which the lines originate; with the angle of intersection of the lines with the fold line extension ranging from about 15° to about 75°.

19. A pad according to claim 18, having a width between 10 and 36 inches and a length between 10 and 40 inches, the length being measured along the edges from which the cuts originate.

20. A pad according to claim 19 wherein the fold line at which said cut indicator lines terminate is placed from one-third to two-thirds of the length of the pad from the edge to which the fold line is generally parallel and which is nearer to the points at which the indicator lines originate.

21. A pad according to claim 20, wherein the angle of intersection of the cut line with the fold line extension is between about 30° and about 60°.

22. A pad of claim 18 wherein said cut indicator lines are embossed.

23. The pad of claim 18 wherein said cut indicator lines are printed.

* * * * *